(12) United States Patent
Sempere et al.

(10) Patent No.: US 8,580,513 B2
(45) Date of Patent: Nov. 12, 2013

(54) METHODS FOR DETERMINING RESPONSE TO NEOADJUVANT THERAPY AND SURVIVAL USING MICRORNA-10B

(75) Inventors: Lorenzo F. Sempere, Lebanon, NH (US); Murray Korc, Hanover, NH (US); Meir Preis, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/172,047

(22) Filed: Jun. 29, 2011

(65) Prior Publication Data
US 2012/0021415 A1    Jan. 26, 2012

Related U.S. Application Data

(63) Continuation-in-part of application No. PCT/US2011/040624, filed on Jun. 16, 2011.

(60) Provisional application No. 61/447,882, filed on Mar. 1, 2011, provisional application No. 61/441,694, filed on Feb. 11, 2011, provisional application No. 61/377,245, filed on Aug. 26, 2010, provisional application No. 61/365,945, filed on Jul. 20, 2010.

(51) Int. Cl.
*C12Q 1/68* (2006.01)

(52) U.S. Cl.
USPC ........................................... 435/6.14

(58) Field of Classification Search
None
See application file for complete search history.

(56) References Cited

U.S. PATENT DOCUMENTS

| 7,670,840 B2 | 3/2010 | Croce et al. | |
| 2006/0003337 A1 | 1/2006 | Brandis et al. | 435/6.14 |
| 2010/0129832 A1 | 5/2010 | Kobayashi et al. | 435/7.4 |

OTHER PUBLICATIONS

Strausberg et al, In Microarrays and Cancer Research, 2002, Warrington et al (eds.), Eaton Publishing, Westborough, MA, pp. xi-xvi.*
Notterman et al, In Microarrays and Cancer Research, 2002, Warrington et al (eds.), Eaton Publishing, Westborough, MA, pp. 81-111.*
Planell-Saguer et al. "Rapid in situ Codetection of Noncoding RNAs and Proteins in Cells and Formalin-Fixed Paraffin-Embedded Tissue Sections Without Protease Treatment" Nature Protocols 2010 vol. 5(6):1061-1073.
Roth, K.A. "Tyramide Signal Amplification Strategies for Fluorescence Labeling" 2008 Department of Pathology, University of Alabama at Birmingham. Birmingham, Alabama. [Retrieved from the Internet Oct. 20, 2011: <http://www.sfn.org/siteobjects/published/0000BDF20016F63800FD712C30FA42DD/2E67345704AE45832EC66118E72A9BD4/file/2%20Roth%20Short%20Course%20Syllabus.pdf>].
International Search Report from PCT Application No. PCT/US2011/040624, Jan. 25, 2012.
Bloomston et al. "MicroRNA Expression Patterns to Differentiate Pancreatic Adenocarcinoma from Normal Pancreas and Chronic Pancreatitis" The Journal of the American Medical Association 2007 297(17):1901-1908.
du Rieu et al. "MicroRNA-21 Is Induced Early in Pancreatic Ductal Adenocarcinoma Precursor Lesions" Clinical Chemistry 2010 56(4):603-612.
Greither et al. "Elevated Expression of MicroRNAs 155, 203, 210, and 222 in Pancreatic Tumors Is Associated with Poorer Survival" International Journal of Cancer 2010 126(1):73-80.
Lee et al. "Expression Profiling Identifies MicroRNA Signature in Pancreatic Cancer" International Journal of Cancer 2007 120(5):1046-1054.
Szafranska et al. "Analysis of MicroRNAs in Pancreatic Fine-Needle Aspirates Can Classify Benign and Malignant Tissues" Clinical Chemistry 2008 54(10):1716-1724.
Zhang et al. "Profiling of 95 MicroRNAs in Pancreatic Cancer Cell Lines and Surgical Specimens by Real Time PCR Analysis" World Journal of Surgery 2009 33(4):698-709.

* cited by examiner

*Primary Examiner* — James Martinell
(74) *Attorney, Agent, or Firm* — Licata & Tyrrell, P.C.

(57) ABSTRACT

The present invention provides methods for determining response to neoadjuvant therapy and metastasis-free survival in pancreatic ductal adenocarcinoma based upon the level of microRNA expression and optionally the presence of a protein cancer cell marker in biological samples such as formalin-fixed paraffin-embedded specimens using in situ hybridization and optionally an immunohistochemical assay.

4 Claims, 3 Drawing Sheets

SEQUENCE LISTING

```
<160> NUMBER OF SEQ ID NOS: 8

<210> SEQ ID NO 1
<211> LENGTH: 110
<212> TYPE: RNA
<213> ORGANISM: Homo sapiens

<400> SEQUENCE: 1
ccagagguug uaacguuguc uauauauacc cuguagaacc gaauuugugu gguauccgua      60
uagucacaga uucgauucua ggggaauaua uggucgaugc aaaaacuuca              110

<210> SEQ ID NO 2
<211> LENGTH: 23
<212> TYPE: RNA
<213> ORGANISM: Homo sapiens

<400> SEQUENCE: 2
uacccuguag aaccgaauuu gug                                            23

<210> SEQ ID NO 3
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 3
cacaaattcg gttctacagg gta                                            23

<210> SEQ ID NO 4
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 4
tcaacatcag tctgataagc ta                                             22

<210> SEQ ID NO 5
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 5
ttaatgctaa tcgtgatagg ggt                                            23

<210> SEQ ID NO 6
<211> LENGTH: 22
<212> TYPE: DNA
<213> ORGANISM: Artificial sequence
<220> FEATURE:
```

```
<223> OTHER INFORMATION: Synthetic oligonucleotide

<400> SEQUENCE: 6
cccaacaaca tgaaactacc ta                                              22

<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 7
tcagccgctg tcacacgcac ag                                              22

<210> SEQ ID NO 8
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 8
cgtgtcatcc ttgcgcaggg gccatgctaa tcttctctgt                           40
```

METHODS FOR DETERMINING RESPONSE TO NEOADJUVANT THERAPY AND SURVIVAL USING MICRORNA-10B

This application is a continuation-in-part application of PCT/US2011/040624, filed Jun. 16, 2011, which claims priority to U.S. Provisional Application No. 61/447,882, filed Mar. 1, 2011; U.S. Provisional Application No. 61/441,694, filed Feb. 11, 2011; U.S. Provisional Application No. 61/377,245, filed Aug. 26, 2010; and U.S. Provisional Application No. 61/365,945, filed Jul. 20, 2010, which are incorporated herein by reference.

INTRODUCTION

This invention was made with government support under grant numbers R21CA133715 and CA-R37-075059 awarded by the National Cancer Institute. The government has certain rights in the invention.

BACKGROUND OF THE INVENTION

MicroRNAs (miRNAs) are a class of short non-coding regulatory RNA genes, which act as post-transcriptional regulators of gene expression (Lee & Ambros (2001) *Science* 294(5543):862-4; Lau, et al. (2001) *Science* 294(5543):858-62; Lagos-Quintana, et al. (2001) *Science* 294(5543):853-8). By binding to the 3'-untranslated region of target mRNAs, the ~21-23 nucleotide-long miRNAs can trigger translational downregulation and/or increased degradation of mRNA of target genes (Bartel (2009) *Cell* 136(2):215-33). The recent explosion of miRNA research in biomedical sciences and particularly in cancer biology attests to their importance to human disease (Ventura & Jacks (2009) *Cell* 136(4):586-91; Sempere & Kauppinen (2009) In: *Handbook of Cell Signaling.* 2nd ed. Oxford: Academic Press, Bradshaw & Dennis (eds.) pg. 2965-81). High-throughput expression profiling of RNA extracted from whole tissue biopsies has provided short lists of miRNAs that could serve as useful biomarkers for early detection, diagnosis and/or prognosis of different types of cancer (Barbarotto, et al. (2008) *Int. J. Cancer* 122(5):969-77). Low levels of let-7, miR-34, miR-126, miR-145 and high levels of miR-21, miR-155, miR-221 have been frequently reported in association with breast, colorectal, gastrointestinal, lung, pancreas, prostate and/or thyroid cancer (Barbarotto, et al. (2008) supra; Volinia, et al. (2006) *Proc. Natl. Acad. Sci. USA* 103(7):2257-61).

Pancreatic ductal adenocarcinoma (PDAC) is the fourth leading cancer-related deaths in the US with an annual mortality of nearly 38,000, a median survival of 6-7 months and a five-year survival rate of 4 to 5% (Bilimoria, et al. (2007) *Cancer* 110(4):738-44). PDAC is characterized by aggressive local invasion, early lymphatic and hematogenous dissemination, and chemotherapeutic resistance (Preis & Korc (2010) *Cancer Biol. Ther.* 9(10):754-63). Tissue diagnosis is most often obtained by Endoscopic Ultrasound-Guided Fine Needle Aspiration (EUS-FNA) sampling of the pancreatic mass or other suspicious lesion (Kahl & Malfertheiner (2004) *Dig. Dis.* 22(1):26-31). Less than 20% of PDAC patients are candidates for surgical resection at diagnosis (Sener, et al. (1999) *J. Am. Coll. Surg.* 189(1):1-7; Lim, et al. (2003) *Ann. Surg.* 237(1):74-85). Despite improved survival with adjuvant chemoradiotherapy following resection, most patients eventually die of their disease (Herman, et al. (2008) *J. Clin. Oncol.* 26(21):3503-10; Corsini, et al. (2008) *J. Clin. Onocol.* 26(21):3511-6; Pipas, et al. (2001) *Int. J. Radiat. Oncol. Biol. Phys.* 50(5):1317-22). The tumor-associated antigen CA 19-9, which may be used adjunctively in the management of patients with PDAC following tumor resection to monitor disease recurrence, cannot predict the metastatic potential of tumor or patient survival following resection (Locker, et al. (2006) *J. Clin. Oncol.* 24(33):5313-27). Conventionally, no tissue biomarkers have been identified to guide therapeutic strategies or predict patient prognosis in PDAC.

The expression of several microRNAs, as determined by quantitative reverse-transcription PCR analysis (qRT-PCR), is altered in PDAC. Among others, miR-21, miR-10b, miR-155, miR-196a, miR-203, miR-210 and miR-221 levels are increased in PDAC by comparison with the normal pancreas (Greither, et al. (2010) *Int. J. Cancer* 126(1):73-80; Bloomston, et al. (2007) *JAMA* 297(17):1901-8; Szafranska, et al. (2008) *Clin. Chem.* 54(10):1716-24; Lee, et al. (2007) *Int. J. Cancer* 120(5):1046-54; du Rieu, et al. (2010) *Clin. Chem.* 56(4):603-12; Zhang, et al. (2009) *World J. Surg.* 33(4): 698-709; U.S. Pat. No. 7,670,840) whereas miR-375 and miR-148 levels are decreased in PDAC (Bloomston, et al. (2007) supra; Hanoun, et al. (2010) *Clin. Chem.* 56(7):1107-18). In general, these studies did not take into account the fact that PDAC is highly desmoplastic, and that the pancreatic tumor mass may include variable amounts of inflammatory cells and mast cells, degenerating acinar cells, proliferating ductal cells, foci of acinar to ductal metaplasia (ADM) and/or pancreatic intraepithelial neoplasia (PanIN), as well as many cancer-associated fibroblasts and stellate cells (Hezel, et al. (2006) *Genes Dev.* 20(10):1218-49). Therefore, the spatial expression of miRNAs in PDAC tissue is needed.

SUMMARY OF THE INVENTION

The present invention includes methods for determining response to neoadjuvant therapy and metastasis-free survival in PDAC. The methods involve the steps of (a) obtaining a biological sample from a patient with PDAC; (b) determining the level of microRNA-10b in the biological sample; and (c) comparing the level of microRNA-10b to a control, wherein the level of microRNA-10b expression relative to the control is indicative of the patient's response to neoadjuvant therapy, e.g., a gemcitabine-based therapy, or metastasis-free survival. In some embodiments, the level of microRNA-10b is determined in combination with the presence of a protein cancer cell marker such as a cytokeratin or mucin. In accordance with said co-detection, it is preferable that the levels of microRNA-10b and protein cancer cell marker are determined by in situ hybridization and immunohistochemical staining, respectively, of a formalin-fixed paraffin-embedded biological sample.

BRIEF DESCRIPTION OF THE DRAWINGS

FIG. 1 shows that levels of miR-10b predict response to multimodality neoadjuvant treatment.

DETAILED DESCRIPTION OF THE INVENTION

Figure 1A:
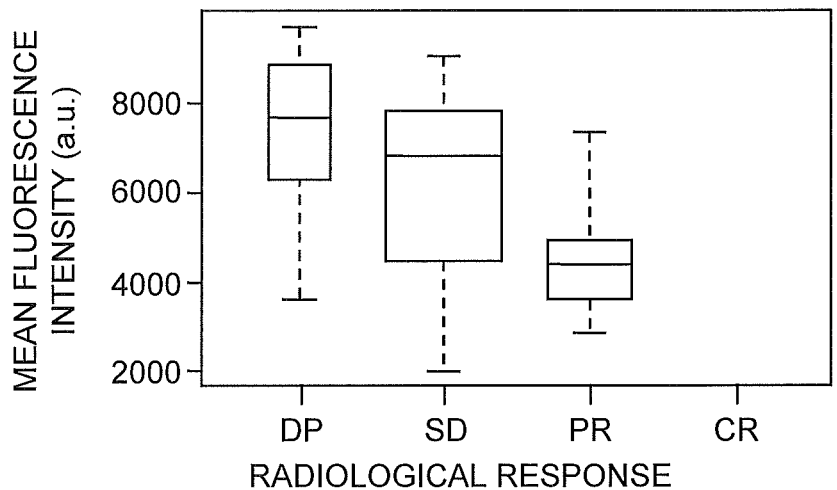
FIG. 1A, Box & whisker plot summarizes data for miR-10b levels in FNA samples (n=44) grouped with respect to radiological response in patients who received multimodality neoadjuvant treatment (Table 1). P=0.0012 for the correlation between miR-10b levels and radiological response.
Figure 1B:
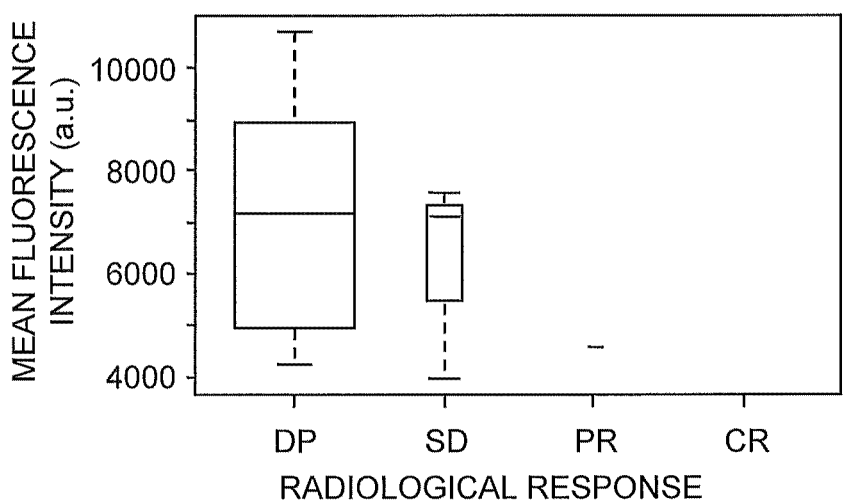
FIG. 1B, Box & whisker plot depicts miR-10b levels in FNA samples (n=18) grouped with respect to radiological response in patients who received palliative gemcitabine-based chemotherapy. DP—disease progression; SD—stable disease; PR—partial response; CR—complete response.

Using resected formalin-fixed paraffin-embedded (FFPE) PDAC tissue samples and benign pancreatic tissue samples, it was observed that there is a strong positive correlation between increased miR-10b expression in the cytokeratin 19 (CK19)-positive cancer cells and shorter time to metastasis, decreased overall patient survival and resistance to multimodality neoadjuvant chemotherapy and radiation. Thus, miR-10b serves as a novel diagnostic and prognostic biomarker in PDAC, and as a tool for predicting response to therapy, in particular neoadjuvant therapy.

Given that low levels of miR-10b in cancer cells is associated with response to neoadjuvant therapy, surgical resectability, time to metastasis and overall survival, the present invention provides methods for determining response to neoadjuvant therapy, in particular a gemcitabine-based therapy, and metastasis-free survival in PDAC based upon the low level of miR-10b expression as compared to controls. Controls include one or more exemplary biological samples representative of low, medium or high levels of miR-10b expression. As described herein, the normal pancreas exhibits weak miR-10b expression. By contrast, in PDAC, there is an abundance of CK19-positive cancer cells that express increased levels of miR-10b; wherein said miR-10b levels can be divided into three levels of fluorescence intensity (i.e., using a fluorescent probe): low <5,000 a.u., intermediate 5,000-7, 999 a.u., and high ≥8,000 a.u. By comparing fluorescence intensity of exemplary control samples with fluorescence intensity of a biological sample from a PDAC patient, the patient can be classified as having relatively low, intermediate or high levels of miR-10b expression.

Neoadjuvant therapy is used to downsize/downstage tumors, thereby improving rates of complete resection, and reducing local relapse rates (Gillen, et al. (2010) *PLoS Med.* 7(4):e1000267. Thus, the identification of patients who could benefit from this early treatment of local disease would improve overall survival. Indeed, as the data herein indicated, those patients whose cancers express low levels of miR-10b were predicted to have greater than 50% survival after 2 years. By contrast, high levels of miR-10b projected poor outcome and early disease progression even after surgical resection.

In accordance with the instant methods, a biological sample is a biopsy or body fluid obtained from a patient with PDAC, wherein said sample contains tumor and/or tumor-associated tissue or cells. Biopsies are small pieces of tissue and may be fresh, frozen or fixed, such as formalin-fixed and paraffin embedded (FFPE). Body fluid samples may be blood, plasma, serum, urine, or ductal fluid samples and may likewise be fresh, frozen or fixed. Samples may be removed surgically, by extraction, i.e., by hypodermic or other types of needles, by microdissection or laser capture. The sample may be a tissue sample as described herein and in certain embodiments is a FFPE sample.

In certain embodiments, it may be desirable to obtain more than one sample, such as two samples, such as three samples, four samples or more from a patient. The at least two samples may be taken from normal tissue and hyperproliferative tissue, respectively. This allows the confirmation of the presence, absence, level of expression, and/or localization of miR-10b between the two samples. Alternatively, a single sample may be compared against control samples, such as samples containing material or data from several samples, preferably also from several patients. Control or standardized samples may depict either various levels miR-10b expression or data representing ranges of fluorescence intensity (e.g., low <5,000 a.u., intermediate 5,000-7,999 a.u., and high ≥8,000 a.u.).

Examination of FFPE tissues is the cornerstone for histological and molecular pathology diagnosis of solid tumors. High-throughput profiling experiments have linked altered expression of miRNAs to different types of cancer. Several methodologies have been applied to detect miRNAs in FFPE specimens. However, tumor tissues are a heterogeneous mixture of not only cancer cells, but also supportive and reactive tumor microenvironment elements. In this respect, in situ hybridization (ISH) assays have the unique feature of determining the cellular compartment(s) of altered miRNA expression, which is demonstrated herein as being paramount to accurately interpreting the clinical significance of miRNA changes.

In this respect, particular embodiments of the instant method encompass in situ detection. The term in situ method refers to the detection of markers in a sample wherein the structure of the sample has been preserved. This may thus be a biopsy wherein the structure of the tissue is preserved. In situ methods are generally histological, i.e., microscopic in nature and include but are not limited to methods such as in situ hybridization techniques and immunohistochemical methods. In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH is used to assay expression and gene expression patterns in a tissue/across cells, such as the expression of miRNAs/nucleic acid molecules as described herein.

In the methods of this invention, the level of miR-10b expression is determined. In human, the pre-miR-10b has the sequence 5'-CCA GAG GUU GUA ACG UUG UCU AUA UAU ACC CUG UAG AAC CGA AUU UGU GUG GUA UCC GUA UAG UCA CAG AUU CGA UUC UAG GGG AAU AUA UGG UCG AUG CAA AAA CUU CA-3' (SEQ ID NO:1) and mature miR-10b has the sequence 5'-UAC CCU GUA GAA CCG AAU UUG UG-3' (SEQ ID NO:2). Levels of miR-10b expression can be determined as exemplified herein using miR-10b specific probes or by other routine methods for detecting nucleic acids in a sample, e.g., northern blot analysis, qRT-PCR and the like. However, as described above, levels of miR-10b expression are determined by in situ hybridization so that the spatial expression of miR-10b is determined.

To detect the level, and optionally localization, of miR-10b, the method of the invention employs a probe. The term "probe" refers to a defined oligonucleotide or a nucleic acid molecule used to detect a target miRNA nucleic acid molecule by hybridization, in particular in situ hybridization. In this respect, a probe bears a complementary sequence to the miR-10b sequence. Probes of the invention can be single-stranded DNA, partially double-stranded DNA, RNA or a combination of DNA and RNA. In some embodiments, the probe of the invention is synthesized or produced with conventional oligonucleotides. In other embodiments, the probe is modified to include chemical modifications.

If present, chemical modifications of a probe can include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylammonium)propyl]carboxyamide)-2'-deoxyuridine chloride, 5-(N-napthylmethylcarboxyamide)-2'-deoxyuridine, 5-(Imidazolylethyl)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, backbone modifications, methylations, unusual base-pairing combinations such as the isobases isocytidine and isoguanidine, and the like.

In one embodiment, 5-position pyrimidine modifications refer to pyrimidines with a modification at the C-5 position. Examples of a C-5 modified pyrimidine include those described in U.S. Pat. Nos. 5,719,273 and 5,945,527. Examples of a C-5 modification include substitution of deoxyuridine at the C-5 position with a substituent selected from benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) In this respect, representative C-5 modified pyrimidines include 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU) and 5-(N-napthylmethylcarboxyamide)-2'-deoxyuridine (NapdU).

Modified probes of the invention include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). In particular embodiments, a modified probe of the invention contains at least one nucleoside analog, e.g., a locked nucleic acid (LNA). The synthesis and preparation of LNA monomers adenine, cytosine, guanine, 5-methyl-cytosine, thymine and uracil, along with their oligomerization, and nucleic acid recognition properties have been described (Koshkin, et al. (1998) *Tetrahedron* 54:3607-3630). LNAs and preparation thereof are also described in WO 98/39352 and WO 99/14226.

Other modifications include 3' and 5' modifications, such as capping. Further, any of the hydroxyl groups ordinarily present in a sugar may be replaced by a phosphonate group or a phosphate group; protected by any suitable protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (C1-C20) optionally containing an ether (—O—) linkage, aryl, alkenyl, cycloalkyl, cycloalkenyl or araldyl. Not all linkages in a probe need be identical. Substitution of analogous forms of sugars, purines, and pyrimidines can be advantageous in designing a final product, as can alternative backbone structures like a polyamide backbone, for example.

If present, a modification to the nucleotide structure of a probe may be imparted before or after assembly of the probe. A sequence of nucleotides may be interrupted by non-nucleotide components. A probe may be further modified after polymerization, such as by conjugation with a labeling component.

In particular embodiments, the probe has a nucleotide sequence of SEQ ID NO:3 or a fragment thereof that can hybridize under stringent condition, and/or has an identity of at least 80% to any of this sequence.

In accordance with the present method, a probe is detected with a label or tag or otherwise modified to facilitate detection. A label or a tag is an entity making it possible to identify a compound to which it is associated. It is within the scope of the present invention to employ probes that are labeled or tagged by any means known in the art such as, but not limited to, radioactive labeling, affinity labeling (e.g., with a hapten and its associated antibody), fluorescent labeling and enzymatic labeling. Furthermore, the probe may be immobilized to facilitate detection. In particular embodiments, a hapten is incorporated into the probe of the invention. Haptens commonly employed in labeling applications include fluorescein (e.g., 5- or 6-carboxy-fluorescein, FAM), biotin, digoxigenin (DIG), 5-bromo-2-deoxyuridine (BrdU) and dinitrophenol.

Probe synthesis and hapten incorporation are routinely practiced in the art and any suitable method can be employed. See, e.g., Luehrsen, et al. (2000) *J. Histochem. Cytochem.* 48:133-145.

Detection of probes with labels as described herein is routinely practiced in the art and any suitable method can be employed. In particular embodiments, the probe contains a hapten that is detectable using an immunoassay. Accordingly, certain embodiments of this invention include the use of an anti-hapten antibody. In this respect, binding of the probe to the miRNA can be detected by contacting the hapten with an anti-hapten antibody, contacting the anti-hapten antibody with a secondary antibody reagent, and detecting the secondary antibody reagent by routine methods as described herein. For the purposes of the present invention, a secondary antibody reagent is composed of an antibody covalently linked to a protein that provides for a detectable signal. Suitable detectable proteins include, but are not limited to, fluorescent proteins, chromogenic proteins, and enzymes that catalyze the production of a product that is luminescent, fluorescent, or colored (e.g., β-galactosidase, luciferase, horse radish peroxidase, alkaline phosphatase, etc.). Suitable fluorescent proteins include, but are not limited to, green fluorescent protein (GFP; Chalfie, et al. (1994) *Science* 263(5148):802-805); enhanced GFP (EGFP; Clontech Laboratories, Inc.); blue fluorescent protein (BFP; Stauber (1998) *Biotechniques* 24(3):462-471; Heim & Tsien (1996) *Curr. Biol.* 6:178-182); enhanced yellow fluorescent protein (EYFP; Clontech Laboratories, Inc.); and the like. Secondary antibodies linked to various enzymes (i.e., enzyme-conjugated) are commercially available from, for example, Sigma and Amersham Life Sciences (Arlington Heights, Ill.). In certain embodiments, horseradish peroxidase-conjugated secondary antibodies are used in the detection steps of the instant method. In particular embodiments, the invention embraces the use of horseradish peroxidase-mediated tyramide signal amplification (TSA) to enhance detection.

As is known in the art, there are a variety of luminescent, fluorescent, or colored substrates for detecting the activity of enzyme-conjugated secondary antibodies, e.g., by microscopy. For example, horseradish peroxidase-labeled secondary antibody is readily detected with 3,3'-Diaminobenzidine (DAB) and as alkaline phosphatase labeled secondary antibody is readily detected with 5-bromo-4-chloro-3'-indolylphosphate p-toluidine salt (BCIP) and nitro-blue tetrazolium chloride (NBT), both of which are commercially available from a variety of sources (e.g., Pierce Chemical Co., Rockford, Ill.). The enzymatic reaction forms an insoluble colored product wherever antigen-antibody complexes occur.

To increase the sensitivity of detecting enzyme-conjugated secondary antibodies, assays based on fluorescence or luminescence are typically employed. Fluorescent compounds containing fluorophores, also known as fluorochromes, have the ability to absorb energy from incident light and emit the energy as light of a longer wavelength and lower energy. Fluorescein and rhodamine, usually in the form of isothiocyanates that can be readily coupled to antigens and antibodies, are most commonly used in the art (Stites, et al. (1994) Basic and Clinical Immunology). Fluorescein absorbs light of 490 nm to 495 nm in wavelength and emits light at 520 nm in wavelength. Tetramethylrhodamine absorbs light of 550 nm in wavelength and emits light at 580 nm in wavelength. Illustrative fluorescence-based substrates are described herein and further include such examples as ELF-97 alkaline phosphatase substrate (Molecular Probes, Inc., Eugene, Oreg.); PBXL-1 and PBXL-3 (phycobilisomes conjugated to streptavidin); and CY substrates. ELF-97 is a nonfluorescent chemical that is digested by alkaline phosphatase to form a fluorescent molecule. Because of turnover of the alkaline phosphatase, use of the ELF-97 substrate results in signal amplification. Illustrative luminescence-based detection reagents include CSPD and CDP star alkaline phosphatase substrates (Roche Molecular Biochemicals, Indianapolis, Ind.); and SUPERSIGNAL horseradish peroxidase substrate (Pierce Chemical Co., Rockford, Ill.).

In addition to miR-10b, certain embodiments feature the codetection of a protein cancer cell marker in the same samples, thereby enabling reproducible assessment of miR-10b expression in the cancer cells within the tumor mass. In some embodiments, the protein cancer cell marker is a cytokeratin such as cytokeratin (CK) 7, CK8, CK18, CK19, and CK20 (Wildi, et al. (1999) *Clin. Cancer Res.* 5:2840; Bouwens, et al. (1995) *J. Histochem. Cytochem.* 43:245-253; Schussler, et al. (1992) *Am. J. Pathol.* 140:559-568) or a mucin such as MUC1, MUC2, MUC5B and MUC6 (Moniaux, et al. (2004) *Br. J. Cancer* 91:1633-1638). Using the method of this invention, the presence, absence, level or localization of protein cancer cell marker can be determined. As is routine in the art, protein markers can be readily detected by a binding agent such as ligand or antibody that specifically binds the protein marker with little to no detectable binding to any other protein in a sample. In particular embodiments, the binding agent is an antibody specific for the protein cancer cell marker including, but not limited to, CK7, CK8, CK18, CK19, CK20, MUC1, MUC4, MUC5B or MUC6. Antibodies to these proteins are known and available from a number of commercial sources.

The detection of the binding agent bound to the CK19 protein is routinely practiced in the art and any suitable method can be employed. For example, where the binding agent is a ligand, said ligand can be labeled or tagged as described herein and detected via an antibody. In embodiments wherein the binding agent is an antibody (i.e., a primary antibody), a secondary antibody reagent (e.g., an enzyme-conjugated secondary antibody) can be used. In accordance with particular embodiments, binding of the primary antibody to the protein cancer cell marker is detected by contacting the primary antibody with an enzyme-conjugated secondary antibody, and detecting enzyme activity by routine methods as described herein. Exemplary enzyme-conjugated antibodies of use in the claimed method include, but are not limited to, horseradish peroxidase-conjugated antibodies and alkaline phosphatase-conjugated antibodies.

As is readily apparent from the results presented herein, miR-10b and a protein cancer cell marker such as CK19 can be detected using different fluorescent substrates and sequential rounds of horseradish peroxidase-mediated tyramide signal amplification. Increased specificity and sensitivity of signal needed to perform ISH with miRNA probes can be achieved by designing fluorescein (FITC)-labeled LNA-modified DNA oligonucleotides (with two terminal hapten moieties, e.g., 5' and 3' FITC-labeled probes) against the full length of the miRNA (20 to 24 nts) with a melting temperature ($T_m$) between 70-75° C. Furthermore, tyramide signal amplification (TSA) reaction, in which horseradish peroxidase (HRP) can be conjugated to an anti-FITC antibody (which binds to the FITC-labeled miRNA probe) activated the tyramide moiety of a fluorescent substrate resulting in a covalent attachment to proteins in the vicinity of the miRNA probe. Using this methodology several miRNA or other RNA species and several protein markers can be codetected on the same tissue section using different fluorescent substrates using a fully-automated staining station. Accordingly, it is contemplated that in addition to miR-10b and a protein cancer cell marker, other markers can be detected in the assessment of PDAC samples, e.g., U6 snRNA.

The invention is described in greater detail by the following non-limiting examples.

Example 1

Materials and Methods

Human Tissue Samples. Paraffin-embedded (FFPE) PDAC tissue blocks and normal pancreas specimens were obtained from archival files. EUS-FNA samples were obtained from patients with suspicious pancreatic lesions after providing informed consent. Tissues were fixed in 10% formalin or ethanol, embedded in paraffin, cut in 4 μm sections, and mounted on positively-charged barrier frame slides. Clinical outcome data were obtained from medical records. Disease response to treatment was defined according to standard RECIST criteria (Eisenhauer, et al. (2009) Eur. J. Cancer 45:228-47). Categories of response included: disease progression (DP), stable disease (SD), partial response (PR), complete response (CR).

Combined in situ Hybridization (ISH) and Immunohistochemical (IHC) Staining. FFPE sections (4 μm thick) were subjected to combined ISH/IHC. For miRNA detection, LNA-modified DNA probes were used. The probes were directed against the full length of the mature miRNA sequence: miR-10b probe, 5'-CA+CAA+ATT+CGG+TT+CTA+CAG+GGTA-3' (SEQ ID NO:3); miR-21 probe, 5'-T+CAA+CAT+CA+GT+CTG+ATA+AG+CTA-3' (SEQ ID NO:4); miR-155 probe, 5'-T+TA+AT+GCT+AAT+CGT+GAT+AG+GG+GT-3' (SEQ ID NO:5); miR-196a probe, 5'-CC+CAA+CAA+CAT+GA+AA+CT+AC+CTA-3' (SEQ ID NO:6); miR-210 probe, 5'-TCA+GCC+GCT+GTC+ACA+CGC+ACAG-3' (SEQ ID NO:7), wherein +N Denotes LNA modified nucleotide. The fluorescent dye FAM was coupled to 5' and 3' terminal Ts (not part of the miRNA complementary sequence) as hapten for antibody detection. In addition, the tissue sections were incubated with biotinylated DNA probe against U6 snRNA, 5'-CGTGTCATCCT-TGCGCAGGGGCCATGCTAATCTTCTCTGT-3' (SEQ ID NO:8). Then, cytokeratin 19 (CK19) and amylase expression was assessed by sequential reactions. CK19 was detected using mouse anti-CK19 (1:200, Biogenex Labs, San Ramon, Calif.) after proteinase-K treatment, and amplified by incubation with goat anti-mouse conjugated to horseradish peroxidase (HRP, 1:500, BIO-RAD Labs, Hercules, Calif.). Tyramide Signal Amplification (TSA) reactions with the appropriate fluorochrome were performed for signal detection, followed by heat-induced epitope retrieval in buffered citrate and incubation with mouse anti-amylase (1:200, Santa Cruz Biotechnology, Santa Cruz, Calif.). Goat anti-mouse conjugated to HRP (1:500, BIO-RAD) was used for amplification followed by TSA reaction with the appropriate fluorochrome for signal detection. Slides were then washed with phosphate-buffered saline-TWEEN (PBST) and mounted with anti-fading PROLONG Gold solution (Invitrogen, Carlsbad, Calif.).

Quantitative Image Analysis. Fluorescent images were captured with a monochrome camera (EXI BLUE, Q Imaging) mounted on an OLYMPUS BX60 microscope. Exposure time was determined by an automated setting using the IMAGEPRO software (Media Cybernetics, Bethesda, Md.) and the same magnification (×200) was used for image acquisition. A monochromatic image was obtained and saved for further analysis. The same field was captured through different filter cubes to record the staining for U6 snRNA (AMCA, Chroma Filter Set 31000), miR-10b (Fluorescein, OLYMPUS Filter Set U-MNIBA), CK19 (rhodamine, Chroma Filter Set SP102V1 or DYLIGHT 594, Chroma Filter Set SP107) and amylase (DYLIGHT680, Chroma Filter Set SP105). Image files were later colorized. CK19-positive cells were marked as AOI (area of interest) using IMAGEPRO software. This AOI was applied on the matched miR-10b images and the fluorescence intensity for miR-10b was calculated using the signal intensity tool in the CK19-positive cells. Background subtraction of auto fluorescence was performed on the same AOI. The corrected (following background subtraction) mean fluorescent intensity (in arbitrary units) was used to present the data.

Statistics. Kruskal-Wallis, and ANOVA were used as appropriate to compare continuous variables (e.g., age, miR-10b expression) between cancer stages. Wilcoxon-Mann-Whitney was used to compare miR-10b expression between PDAC and benign patients. Kruskal-Wallis, t-tests and ANOVA were used as appropriate to compare continuous characteristics across stages. miR-10b expression in the tissue samples was analyzed based on three levels of fluorescence intensity: low <5,000 a.u., intermediate 5,000-7,999 a.u., high ≥8,000 a.u. The utility of differential miR-10b expression for predicting response was tested using ordinal logistic regression (proportional odds Wald test), while its ability to predict suitability for surgery following induction chemotherapy was tested using logistic regression. Overall survival and metastatic-free survival curves were subjected to Kaplan-Meier analysis and stratified by categories of miR-10b signal intensity. Cox's model was employed to estimate hazard ratios for the association of miR-10b with survival and metastatic-free survival. $p<0.05$ was taken as statistically significant.

Example 2

MicroRNA Expression in PDAC and Normal Pancreatic Tissue

To determine the predominant cell-type responsible for deregulated expression of PDAC-associated miRNAs, the spatial distribution of miR-10b, miR-21, miR-155, miR-196a and miR-210 were characterized by fluorescence-based ISH assay in PDAC tissues and adjacent normal tissues. The same tissue sections were immunostained for CK19, a ductal cell marker in the normal pancreas and a cancer cell marker in PDAC, and for amylase, an acinar cell marker. The fluorescence intensity of each miRNA was determined in the CK19-positive cells in resected PDACs (n=10) and in benign pancreatic tissues (n=3). In the normal pancreas, Haematoxylin Eosin (H&E) staining revealed an abundance of amylase-positive acinar cells, and a few CK19-positive ductal cells, and both cell types exhibited a weak miR-10b signal. By contrast, in PDAC, there was an abundance of CK19-positive cancer cells that expressed high levels of miR-10b. Among the five tested miRNAs, miR-10b was the most frequently and consistently overexpressed miRNA within cancer cells, exhibiting a four-fold increase in the cancer cells when compared with miR-10b levels in CK19-positive cells from normal pancreatic tissues (p=0.012).

PDACs often harbor chronic pancreatitis-like changes with foci of atrophic acinar cells and proliferating ductal cells, and both cell types may overexpress signaling molecules (Kloppel, et al. (2009) Pathol. Lab Med. 133:382-7). It was therefore determined whether there was differential expression of miR-10b in cancer cells by comparison with the adjoining, non-malignant CK19-positive cells, using a different set of surgical specimens (n=8). The mean fluorescence intensity in the CK19-positive cancer cells was significantly higher when compared with CK19-positive cells from the adjoining normal appearing pancreas (3642±1322 vs. 733±394 a.u.; p=0.006), with one PDAC sample not exhibiting high miR-10b levels.

Example 3

MiR-10b Expression in EUS-FNA Samples from Suspicious Pancreatic Lesions

EUS-FNA sampling from a suspicious pancreatic mass is useful for diagnosing PDAC. To investigate whether miR-10b detection by ISH could be informative for guiding therapeutic intervention, EUS-FNA samples were obtained from 155 patients with suspicious pancreatic lesions. PDAC was diagnosed in 95/155 cases by light microscopy and benign cytology was suggested in 11/155 cases. The remaining 49 cases, which were not included in this study were diagnosed as intraductal papillary mucinous neoplasm (11 cases), neuroendocrine tumors (20 cases), and other non-pancreatic malignancies (11 cases). In 7 cases, the pathological diagnosis was undetermined.

In the benign lesions, the CK19-positive epithelial cells exhibited a weak miR-10b signal, which was also evident in the pancreatic acinar cells. In the FNA samples obtained from patients with PDAC, CK19-positive cells exhibited a strong and intense miR-10b signal. Based on the analysis of miR-10b expression in the CK19-positive cells, miR-10b expression was significantly elevated in the samples that were subsequently diagnosed as PDAC, when compared with miR-10b expression in samples from benign lesions (6291±2251 vs. 1249±921 a.u.; p=0.0001).

Example 4

Clinical Utility of miR-10b Measurement in FNA Samples

The clinical characteristics (including age, mass size, and CA 19-9 antigen levels) of the patients diagnosed with PDAC are described in Table 1 (Callery, et al. (2009) *Ann. Surg. Oncol.* 16:1727-33).

TABLE 1

|  | Stage I (n = 16) | Stage II (n = 33) | Stage III (n = 18) | Stage IV (n = 28) |
|---|---|---|---|---|
| Age (y)[1] | 72 ± 12 | 68 ± 12 | 68 ± 11 | 66 ± 10 |
| Mass size (mm)[2] | 24 ± 7 | 28 ± 7 | 42 ± 10 | 40 ± 17 |
| CA 19-9 µ/ml (median, range)[3] | 131, 5-2,498 | 230, 6->10,000 | 190, 5->10,000 | 473, 5->10,000 |
| Normal CA 19-9 (≤35 µ/ml) | 12% (2/16) | 11% (3/27) | 30% (4/13) | 10% (2/20) |
| miR-10b (a · u) | 5759 ± 2335 | 5947 ± 2248 | 6672 ± 2060 | 6759 ± 2306 |
| Low miR-10b (<5000 a · u)[4] | 50% (8/16) | 45% (15/33) | 22% (4/18) | 36% (10/28) |
| Treatment choices: |  |  |  |  |
| Surgery alone (%) | 0 | 0 | 0 | 0 |
| Surgery + adjuvant chemotherapy | 1/16 | 2/33 | 0 | 0 |
| Induction Chemo-RTx, no surgery | 4/16 | 12/33 | 10/18 | 0 |
| Induction Chemo-RTx and surgery | 7/16 | 14/33 | 2/18 | 0 |
| Palliative chemotherapy | 0 | 0 | 4/18 | 19/28 |
| Best supportive care/unknown | 4/16 | 5/33 | 2/18 | 9/28 |
| Median survival | 16 | 12 | 8 | 3 |

[1] p Value = 0.28.
[2] p Value = 0.244.
[3] p Value = 0.56.
[4] p Value = 0.33.

Patients with stage I disease had the longest median survival, whereas patients with stage 1V disease had the shortest median survival. At Dartmouth-Hitchcock Medical Center, patients with PDAC, but no evidence of metastatic disease, are generally offered a combined modality approach with neoadjuvant gemcitabine-based chemoradiotherapy followed by attempted resection (Pipas, et al. (2001) supra; Pipas, et al. (2005) *Ann. Surg. Oncol.* 12:995-1004). Forty-nine patients were treated with a multimodality neoadjuvant approach with the intention to follow with surgery, but only 23 of these patients underwent tumor resection (Table 1). None of the patients had surgery alone as a treatment modality (Table 1), and only three patients had surgery followed by adjuvant chemotherapy (Table 1). Patients with metastatic disease or with advanced disease that were not candidates for surgical resection were preferentially treated with palliative gemcitabine and/or best supportive care.

Correlation of miR-10b measurements to clinical outcome was assessed retrospectively following determination of the mean fluorescence intensity for miR-10b. In patients with resectable or locally advanced disease, relatively low miR-10b expression was highly predictive of response to neoadjuvant, gemcitabine-based chemoradiotherapy (n=44, P=0.0012). In addition, low miR-10b expression predicted tumor resectability and surgery with curative intent (P=0.0162 by logistic regression). Each 1,000 a.u. increase in the mean fluorescence intensity of miR-10b correlated with an average 7% (2-13%) decrease in likelihood of surgical resection. By contrast, miR-10b levels did not correlate with response in patients with metastatic disease treated with gemcitabine-based, palliative chemotherapy (n=18, p=0.26).

Figure 2A:
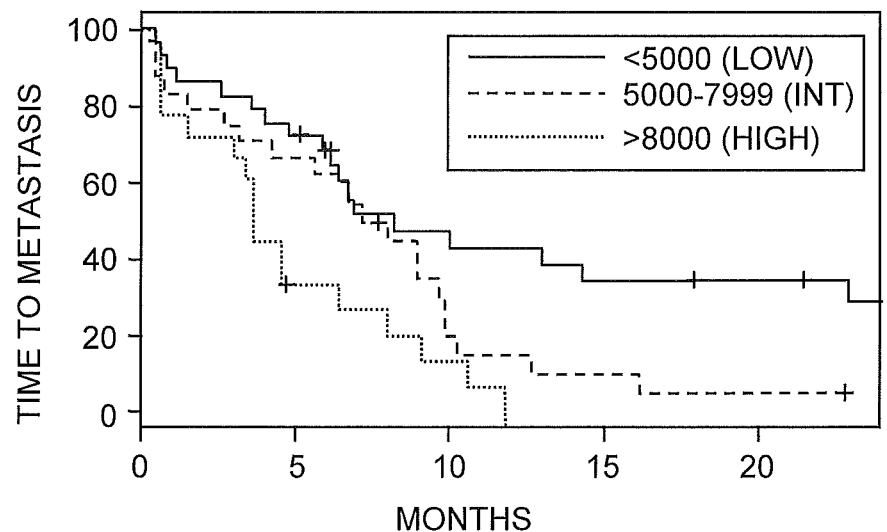
FIG. 2 shows the correlation between levels of miR-10b and time to metastasis. miR-10b expression was characterized in 95 EUS-FNA samples from PDAC patients. EUS- FNA samples were classified as having low (<5000 absorbance units (a.u.)), intermediate (5000-7999 a.u.) and high (>8000 a.u.) levels of miR-10b expression. Kaplan-Meier plots display time to metastasis based on different levels of miR-10b expression for all patients (FIG. 2A), or for patients grouped by stage at diagnosis (Stage I and II, FIG. 2B; Stage III, FIG. 2C). The median time for progression to metastatic disease (3.7 months) was significantly shorter (p=0.001) in patients with high miR-10b expression compared to patients with intermediate (7.1 months) or low levels of expression (8.1 months).
Figure 2B:
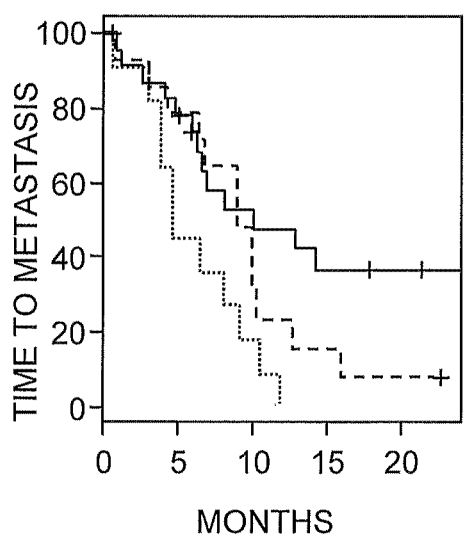
Figure 2C:
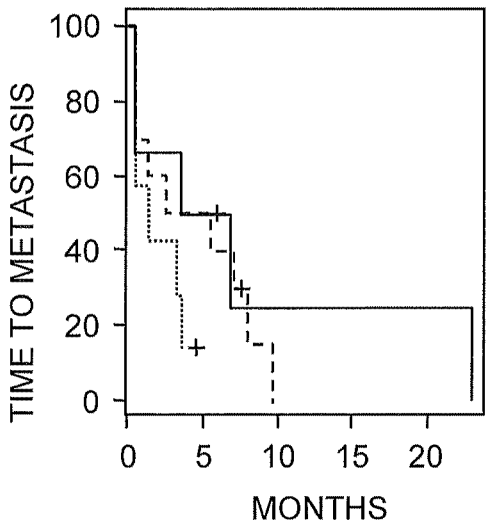

To assess correlation with metastasis-free survival, miR-10b expression was analyzed based on three levels of fluorescence intensity: low <5,000 a.u., intermediate 5,000-7,999 a.u., or high ≥8,000 a.u. (FIG. 2). The median time for progression to metastatic disease was significantly shorter in the patient with high miR-10b expression (3.7 months) compared to patients with intermediate (7.1 months) or low (8.1 months) levels of expression (FIG. 2A, p=0.001). The difference was significant in stages I (FIG. 2B) and II (FIG. 2C) (hazard ratio, 3.3 for high vs. low miR-10b levels; 95% CI, 1.4-7.78; p=0.0055). All patients with high levels of miR-10b developed metastatic disease within 12 months, whereas approximately one-third of patients with low miR-10b levels were alive and free of metastasis after 24 months.

Figure 3A:
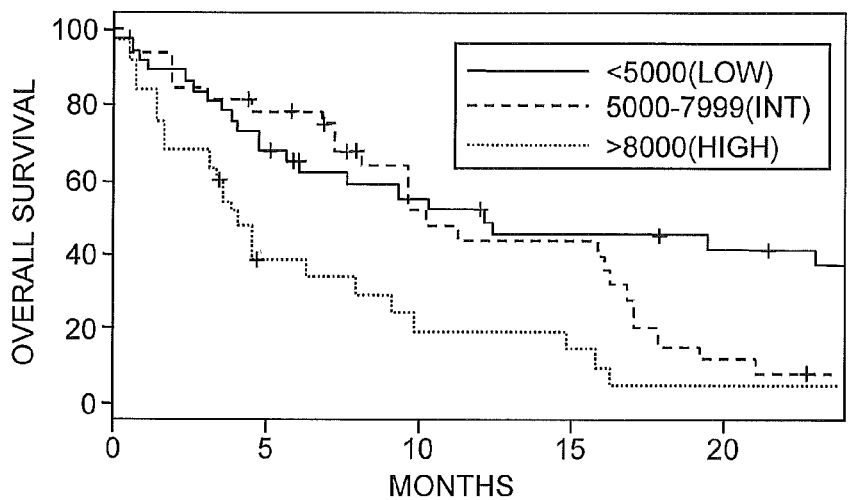
FIG. 3 shows that levels of miR-10b negatively correlate with overall survival. miR-10b expression was characterized in 95 EUS-FNA samples from PDAC patients. Kaplan-Meier plots display overall survival curves based on different levels of miR-10b expression: low (<5000 a.u.), intermediate (5000-7999 a.u.) and high (>8000 a.u.) for all patients (FIG. 3A), or for patients grouped by Stage at diagnosis (Stage I and II, FIG. 3B; Stage III and IV, FIG. 3C). In patients with stage I or II disease at diagnosis, high levels of miR-10b were associated with decreased survival compared to the patients with low levels of miR-10b (p=0.0032).
FIG. 3D, Kaplan-Meier plots display overall survival curves based on different levels of miR-10b expression for patients who received induction chemo-radiation followed by surgery as treatment modality. Patients with high miR-10b expression in the FNA samples had shorter survival by comparison to patients with low miR-10b levels (p=0.0066).
Figure 3B:
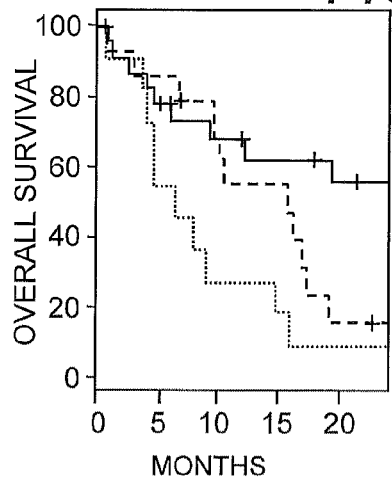
Figure 3C:
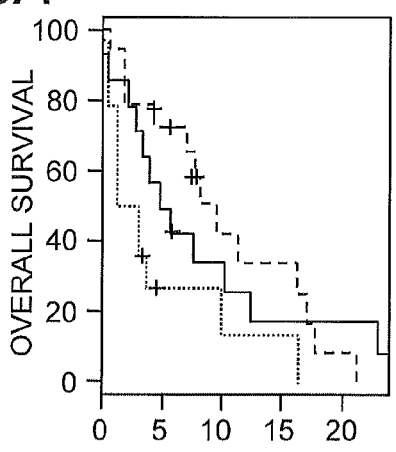
Figure 3D:
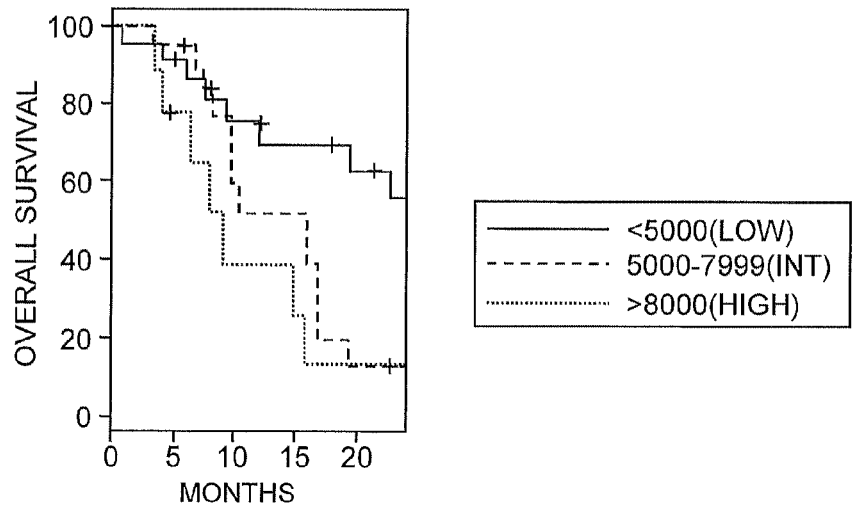

A comparison of survival between patients with low and high miR-10b levels demonstrated that miR-10b significantly predicted survival (p=0.0003, as a continuous marker). The median survival in the low, intermediate and high miR-10b expression groups was 12.1 months, 10.2 months and 4.04 months, respectively (FIG. 3A). The hazard ratio (HR) of miR-10b expression in the high vs. low group was 3.1 (95% CI, 1.66-5.77; p=0.0003). By contrast, there was no significant difference between the intermediate and low miR-10b expressing groups (p=0.11). In patients with stage I or II disease at diagnosis (FIG. 3B), but not in stage III or IV (FIG. 3C), high levels of miR-10b were associated with decreased survival compared to the patients with low miR-10b levels (HR, 3.86; 95% CI, 1.55-9.65; p=0.0032). Moreover, in patients who received multimodality neoadjuvant treatment followed by complete surgical resection, low miR-10b levels at diagnosis were associated with a statistically significant increase in survival compared with patients who had high miR-10b levels (FIG. 3D) (HR, 4; 95% CI, 1.44-11.1; p=0.0066).

What is claimed is:

1. A method for determining response to neoadjuvant therapy in pancreatic ductal adenocarcinoma (PDAC) comprising
   (a) obtaining a biological sample from a patient with PDAC;
   (b) determining the level of microRNA-10b in the biological sample with a microRNA-10b specific probe having the sequence 5'-CA+CAA+ATT+CGG+TT+CTA+CAG+GGTA-3' (SEQ ID NO:3), wherein +N denotes a locked nucleic acid modified nucleotide;
   (c) comparing the level of microRNA-10b in the biological sample to control samples expressing relatively low, medium or high levels of microRNA-10b; and
   (d) diagnosing response of the patient to neoadjuvant therapy, wherein a level of microRNA-10b expression in the biological sample comparable to the control sample expressing a relatively low level of microRNA-10b indicates that the patient is likely to respond to neoadjuvant therapy.

2. A method for determining response to neoadjuvant therapy in pancreatic ductal adenocarcinoma (PDAC) comprising
   (a) obtaining a biological sample from a patient with PDAC;
   (b) detecting cytokeratin or mucin cancer cell marker-positive cells of the biological sample;
   (c) determining the level of microRNA-10b in the cytokeratin or mucin cancer cell marker-positive cells;
   (d) comparing the level of microRNA-10b in the cytokeratin or mucin cancer cell marker-positive cells to control cells expressing relatively low, medium or high levels of microRNA-10b; and
   (e) diagnosing response of the patient to neoadjuvant therapy, wherein a level of microRNA-10b expression in the cytokeratin or mucin cancer cell marker-positive cells comparable to the control sample expressing a relatively low level of microRNA-10b indicates that the patient is likely to respond to neoadjuvant therapy.

3. A method for determining metastasis-free survival in pancreatic ductal adenocarcinoma (PDAC) comprising
   (a) obtaining a biological sample from a patient with PDAC;
   (b) determining the level of microRNA-10b in the biological sample with a microRNA-10b specific probe having the sequence 5'-CA+CAA+ATT+CGG+TT+CTA+CAG+GGTA-3' (SEQ ID NO:3), wherein +N denotes a locked nucleic acid modified nucleotide;
   (c) comparing the level of microRNA-10b in the biological sample to control samples expressing relatively low, medium or high levels of microRNA-10b; and
   (d) diagnosing metastasis-free survival of the patient, wherein a level of microRNA-10b expression in the biological sample comparable to the control sample expressing a relatively low level of microRNA-10b indicates that the patient has an increase in metastasis-free survival.

4. A method for determining metastasis-free survival in pancreatic ductal adenocarcinoma (PDAC) comprising
   (a) obtaining a biological sample from a patient with PDAC;
   (b) detecting cytokeratin or mucin cancer cell marker-positive cells of the biological sample;
   (c) determining the level of microRNA-10b in the cytokeratin or mucin cancer cell marker-positive cells;
   (d) comparing the level of microRNA-10b in the cytokeratin or mucin cancer cell marker-positive cells to control cells expressing relatively low, medium or high levels of microRNA-10b; and
   (e) diagnosing metastasis-free survival of the patient, wherein a level of microRNA-10b expression in the biological sample comparable to the control sample expressing a relatively low level of microRNA-10b indicates that the patient has an increase in metastasis-free survival.

* * * * *